United States Patent
Savransky et al.

(10) Patent No.: US 10,577,578 B2
(45) Date of Patent: Mar. 3, 2020

(54) METHOD FOR DEVELOPING MALARIA SPOROZOITES IN VITRO

(71) Applicants: WALTER REED ARMY INSTITUTE OF RESEARCH DEPARTMENT OF THE ARMY, Washington, DC (US); Tatyana Savransky, Rockville, MD (US); Jackie Williams, Taft, TN (US)

(72) Inventors: Tatyana Savransky, Rockville, MD (US); Jackie Williams, Taft, TN (US)

(73) Assignee: The Government of the United States as represented By the Secretary of the Army, Fort Detrick, MD (US)

( * ) Notice: Subject to any disclaimer, the term of this patent is extended or adjusted under 35 U.S.C. 154(b) by 103 days.

(21) Appl. No.: 15/553,328

(22) PCT Filed: Mar. 10, 2016

(86) PCT No.: PCT/US2016/021743
§ 371 (c)(1),
(2) Date: Aug. 24, 2017

(87) PCT Pub. No.: WO2016/145176
PCT Pub. Date: Sep. 15, 2016

(65) Prior Publication Data
US 2018/0155672 A1    Jun. 7, 2018

Related U.S. Application Data

(60) Provisional application No. 62/131,444, filed on Mar. 11, 2015.

(51) Int. Cl.
C12N 1/10    (2006.01)
C12N 13/00   (2006.01)
C12N 3/00    (2006.01)

(52) U.S. Cl.
CPC ............. *C12N 1/10* (2013.01); *C12N 3/00* (2013.01); *C12N 13/00* (2013.01)

(58) Field of Classification Search
CPC ............ C12N 1/10; C12N 13/00; C12N 3/00
See application file for complete search history.

(56) References Cited

PUBLICATIONS

Kennedy et al.: A rapid and scalable density gradient purification method for Plasmodium sporozoites. Malaria Journal, 2012, 11:421, pp. 1-10.*
Robert Ménard (ed.), 2013, Malaria: Methods and Protocols, Methods in Molecular Biology, vol. 923, Springer Science+Business Media, LLC 2013, 626 pages, p. 17-33 and 580 Only.*
Gosh et al., Malaria Journal, 2010, vol. 9, No. 194, p. 1-7.*
International Search Report, dated Aug. 8, 2016, issued in parent PCT application PCT/US2016/021743, 2 pages.
Chevalley et al., "Flow cytometry for the evaluation of Antiplasmodial activity of drugs . . . ", Malar.J. Feb. 11, 2010, vol. 9:49, pp. 1-7.
Teirlinck et al., "Longevity and compsition of cellular immune responses following experimental Plasmodium . . . " PLoS Pathog., Dec. 1, 2011, vol. 7:e1022389, pp. 1-12.
Al-Olayan et al., "Complete development of mosquito phases of the malaria parasite in vivo," Science, Jan. 25, 2002, Vol. 295, pp. 677-9.
Ifediba et al., "Complete in vitro maturation of Plasmodium falciparum gametocytes," Nature, Nov. 26, 1981, vol. 294, pp. 364-6.
Kennedy et al., "A rapid and scalable density gradient purification method for Plasmodium sporozoites," Malar.J. Dec. 17, 2012, vol. 11:421, pp. 1-10.
Sattabongkot J. et al., 2006, Am.J. Trop. Med. Hyg. 74:708-15.
Warburg and Schneider, Emperimental Parasitology 76, 121-126 (1993).
Zolg, et al., 1982, J. Parasitol. 68, 1072-1080.
McLean, et al., Am. J. Trop. Med. Hyg., 83(6), 2010, pp. 1183-1186.
Ribaut et al., Malaria Journal 2008, 7:45 doi:10.1186/1475-2875-7-45 (Mar. 5, 2008).
Trager, W and Jensen, JB, 1976, Science 193:673-5.
Williams, Am. J. Trop. Med. Hyg., 60(1), 1999, pp. 7-13.
Linthicum, D.S. and Farid, N.R., Anti-Idiotypes, Receptors, and Molecular Mimicry (1988), Chap. 18 (by Y. Thanavala), pp. 285-300.

* cited by examiner

*Primary Examiner* — Kade Ariani
(74) *Attorney, Agent, or Firm* — Leigh Callander (57) ABSTRACT

Described in this application is a method for producing *Plasmodium* sporozoites in a cell-free, mosquito-free in vitro culture-system. Compositions and methods resulting from applying the methods of the present invention are described.

8 Claims, 1 Drawing Sheet

METHOD FOR DEVELOPING MALARIA SPOROZOITES IN VITRO

INTRODUCTION

The malaria sporozoite is the parasite life stage ejected by mosquitoes and the first to enter a human host. There is much interest in developing drugs and vaccines again, sporozoites. The Gates Foundation is actively supporting development of live attenuated sporozoite-based malaria vaccines through a Grand Challenges in Global Health initiative in collaboration with Sanaria, Inc. (Rockville, Md.) and the PATH Malaria Vaccine Initiative. Sanaria's primary approach is to develop a metabolically active, non-replicating (attenuated) malaria sporozoite vaccine candidate. The sporozoites used as a vaccine candidate are isolated from dissected salivary glands of aseptically grown mosquitoes. Needless to say, this current method of sporozoite production is technically difficult, expensive, time consuming, and labor intensive. The ability to produce the sporozoites in vitro would dramatically change the paradigm for producing live attenuated malaria vaccine candidates by completely by-passing the mosquito stage of parasite development.

The desire to grow human infected malaria sporozoites without the mosquito stage began thirty years ago. In 1993, Dr. Imogene Schneider and Dr. Alan Warburg first reported the success of producing live sporozoites using *Drosophila melanogaster* L2 cells (Experimental Parasitology 76, 121-126). Although this method demonstrated the principal possibility of growing sporozoites in vitro, their complex multistage process is unsuitable for production of sporozoites on a large scale.

Therefore, there is a need for a simple, scalable method for in vitro development of a mosquito-stage malaria parasite without using a live insect or insect cells.

SUMMARY OF THE INVENTION

The present invention satisfies the need discussed above. In this application is described a method for producing sporozoites in vitro in a mosquito free, cell free environment. Even though sporozoites are the end stage, all parasite stages produced in the mosquito occur in culture since it is a sequential transition from gametocyte to zygote to ookinete to oocyst to sporozoite. This method will drastically improve the cost, time and feasibility of producing parasite stages used for vaccine development, drug screening and basic biological research pertaining to an important but complex agent of human disease.

Briefly, the method of the present invention is based on isolating gametocytes, for example, from a maintained *P. falciparum* human erythrocytes culture, enriching the gametocyte culture, maturing the gametocytes, and progressing the gametocytes to sporozoites by exflagellation initiated by addition of xanthurenic acid (XA).

XA is a gametocyte activating factor produced in the mosquito midgut and known to induce fertilization. Within human circulation merozoites undergo asexual reproduction where they develop into mature schizonts, which rupture, releasing newly formed merozoites that then reinvade other red blood cells. Some of these merozoite-infected red blood cells leave the cycle of asexual replication and develop into *Plasmodium* gametocytes, male and female sexual forms of the parasite. Normally, when a mosquito bites an infected human, it ingests merozoite-infected red blood cells. In the mosquito midgut, these infected human red blood cells burst, releasing the gametocytes which, in the presence of XA, exflagellate and fuse to form diploid zygotes, which develop into actively moving ookinetes that burrow through the mosquito midgut wall and form oocysts on the other side. Growth and division of each oocyst produces thousands of active haploid forms called sporozoites. After 8-15 days, the oocyst bursts, releasing sporozoites into the body cavity of the mosquito, from which they travel to and invade the mosquito salivary glands. The cycle of human infection re-starts when the mosquito takes a blood meal, injecting the sporozoites from its salivary glands into the human bloodstream. The sporozoites travel to the liver and invade liver cells, developing into merozoites which exit the liver cells and enter the bloodstream.

The present invention is novel in that it diverges from known and accepted methods for growing parasites. For example, if one were mimicking the biological development of sporozoites by following the man-to-mosquito parasite transmission, one would expect to replicate the natural maturation of gametocytes by holding gametocytes in vitro at 37° C. (body temperature) then adding XA and incubating at 27° C. (generalized mosquito body temperature). However, the present method goes against the expected teaching in the art by adding XA and incubating at 37° C. for another 24 hours; only then is the culture moved to 27° C. Therefore, the present method decouples the in vivo observed XA addition and temperature change. Additionally, instead of incubating the developing *Plasmodium* culture under atmospheric air or within a $CO_2$ incubator with air exchange between flask and incubator as is known in the art, the incubation is done in a closed flask environment that is directly provided an initial specific gas mixture and then closed off for the duration of growth.

Further, instead of the traditional method of applying XA transiently then pelleting the parasites and resuspending in fresh media, the present method differs in that the culture is left as-is after XA addition, i.e. the XA is never removed from the culture.

Using the method of the invention, insect-free in vitro-grown *Plasmodium* sporozoites which have never been exposed to an insect or an insect cell can be isolated, and the resulting isolated sporozoite composition contains no insect material, or zero percent contamination from any insect material.

Therefore, it is one object of the present invention to provide a novel method for the production of isolated, live, infectious, metabolically active, sporozoites, or another desired parasite stage, free of any insect material from mosquito salivary gland or insect cells. Briefly, the method comprises isolating *Plasmodium* gametocytes, incubating the gametocytes in the presence of XA until sporozoites are observed, and isolating the sporozoites. The isolated, infectious, metabolically active sporozoites can be used in the identification of parasite stage-specific surface markers, gene expression, protein-protein interactions and other elements of parasite biology that have remained difficult to determine because these lifecycle stages have previously only been reliably produced inside the natural mosquito vector. The present invention makes these stages available for all of these objectives in an aseptic, sterile, clean, reproducible, cost-effective, and scalable way that is independent of the mosquito and the variability inherent in an in vivo system.

It is another object of the present invention to provide mosquito-stage *P. falciparum* produced in vitro for use in producing an attenuated malaria vaccine. Mosquito stage is sporozoites could themselves represent an attenuated sporozoite vaccine, or in addition, the method can serve as an in vitro culturing system to produce malaria vaccine candidates attenuated by other means such as gene knock out or irradiation.

It is yet another object of the invention to provide mosquito-stage *P. falciparum* produced as a source of specific stage DNA and protein. DNA and/or protein can be used as a potential vaccine, or as a tool for gaining insight into production of effective DNA-based and/or antigen-based vaccines. Once identified, the vaccine and/or drug candidates can be tested for efficacy using the in vitro grown sporozoites.

It is yet another object of the invention to provide mosquito-stage *P. falciparum* produced in vitro for use in diagnostic assays, for identifying surface markers related to the specific stage of *P. falciparum*, as well as to provide kits for diagnostic use for example in malaria screening and confirmatory antibody tests.

It is another object of the present invention to provide an antigen source or substrate for producing monoclonal or polyclonal antibodies which react specifically with an antigen from a stage-specific parasite, e.g. sporozoite, zygote, gametocyte, ookinete, oocyst.

It is also an object of the present invention to provide monoclonal or polyclonal antibodies, more particularly human monoclonal antibodies or mouse monoclonal antibodies which are humanized, which react specifically with sporozoite-specific, or stage-specific, antigens, either comprised in peptides or conformational epitopes comprised in recombinant proteins. These monoclonal antibodies can be used as a diagnostic to detect the presence of the parasite or as a therapeutic to reduce disease severity, symptoms, or pathology.

It is still another object of the present invention to provide mosquito-stage *P. falciparum* produced in vitro for use in high-throughput drug screening assays. This in vitro culture system could be developed as a drug screening assay to measure the efficacy of drugs on inhibiting any parasite stage that occurs in the mosquito or the pre-erythrocytic stages (transmitted sporozoites) in humans. This method can also be used for rapid screening of anti-malarial compounds and aid in the discovery of new anti-malaria drugs to protect and/or treat subjects exposed to malaria. A high-throughput, bioassay could be developed to assess such antiparasitic effects and the mechanisms of such inhibition. To assess parasite productivity by microscopic examination is extremely tedious, therefore the screening assay can be linked with a reporter such as either SYBR Green I drug screen or ATP bioluminescence assay. The method described in this invention uniquely allows for SYBR Green- and ATP bioluminescence-based assays that would otherwise be inhibited by background *Drosophila* cell fluorescence when using the Schneider and Warburg method.

The present invention also provides vectors for the production of a recombinant polynucleotide or polypeptide derived from a stage-specific parasite genome, host cells containing the vectors, and a method for isolating and purifying the recombinant polynucleotide or polypeptide produced in the host cells.

All the objects of the present invention are considered to have been met by the embodiments as set out below.

BRIEF DESCRIPTION OF THE DRAWINGS

The figure: Culture flow diagram (also referred to herein as "FIG. 1").

DETAILED DESCRIPTION

In the description that follows, a number of terms used in recombinant DNA, parasitology and immunology are extensively utilized. In order to provide a clearer and consistent understanding of the specification and claims, including the scope to be given such terms, the following definitions are provided.

The terms "about" or "approximately" mean within one standard deviation as per the practice in the art.

The term "aseptic" as used herein means absent the introduction of detectable contamination of other microorganisms such as bacteria, fungi, pathologic viruses and the like. An aseptic method of sporozoite preparation results in a sterile preparation of sporozoites, free of any other type of microorganism or infectious agent. Microbiological assays used to monitor an aseptic methodology assess the presence or absence of contamination. They include, but are not limited to, the Microbial Limits Test, and other tests known to persons in the art.

The term "sporozoite" refers to the infectious form of the malaria parasite which is injected into humans by mosquitoes. Sporozoites are haploid forms that form inside oocysts in the midgut of the mosquito. When the oocyst bursts inside the body, it releases sporozoites into the body cavity of the mosquito, from which they travel to and invade the mosquito salivary glands. The mosquito injects the sporozoites from its salivary glands into the human bloodstream when the mosquito takes a blood meal.

The term "gametocytes" refers to the stage of parasites taken up by the mosquito during blood feeding and are precursors of the sexual forms of the malaria parasite, the male or female gametes. Inside the mosquito gut, the male fertilizes the female, creating a diploid zygote.

The "zygote" transitions to an "ookinete", a motile form of the parasite which moves through the mosquito gut cells to then transition to an "oocyst", a form that sits on the outside of the mosquito midgut and within which the sporozoites develop. The oocyst bursts open to release the sporozoites into the mosquito circulation where they can find and invade the salivary glands in preparation for transmission.

The term "non-parasite" material as used herein means material in a crude preparation of parasites which is not specific to the parasites per se. For example in a preparation of sporozoites, non-parasite material is that which is not specific to the sporozoite per se. Non-parasite material includes material specific to the source from which sporozoites were grown or produced, particularly biological debris, more particularly protein, said material isolated along with the sporozoites in a crude preparation. That which makes a preparation "crude" is the non-parasite material in the preparation, and with regard to sporozoites, includes material specific to the substrate from which the sporozoites have developed or from which the sporozoites have been isolated. With regard to sporozoites dissected from and isolated from the salivary glands of host mosquitoes, non-parasite material is the host material, host protein, salivary gland material, saliva and the like. Non-parasite material does not include components which have been intentionally added to a preparation, e.g., excipient, diluent, additives and the like. In some embodiments, a component of non-parasite material which has been removed from a crude preparation may be added back to the purified preparation to optimize sporozoite infectivity sporozoite immunogenicity, or sporozoite presentation to the host. Such added back material is not considered non-parasite as defined herein.

The term "metabolically active" as used herein means alive, and capable of performing sustentative functions and some life-cycle processes. With regard to sporozoites this includes but is not limited to sporozoites capable of invading hepatocytes in culture and in vivo, potentially having a limited capacity to divide and progress through some developmental stages, and de novo expressing stage-specific proteins.

The term "purify" as defined herein and with regard to preparations of sporozoites, means to separate from non-parasite material or to separate from material considered to be undesirable.

The term "biological sample" intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. falciparum* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term "biological fluid" refers to a fluid obtained from an organism. Some biological fluids are used as a source of other products, such as clotting factors (e.g. Factor VIII), serum albumin, growth hormone and the like.

The term "immunologically reactive" means that the antigen in question will react specifically with antibodies specific for said antigen present in a solution.

The term "immune complex" intends the combination formed when an antibody binds to an epitope on an antigen.

The term "purified" as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein.

The term "essentially purified proteins" refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term "recombinantly expressed" used within the context of the present invention refers to proteins that are produced by recombinant expression methods be it in prokaryotes, or lower or higher eukaryotes as discussed in detail below.

The term "lower eukaryote" refers to host cells such as yeast, fungi and the like. Lower eukaryotes are generally (but not necessarily) unicellular. Preferred lower eukaryotes are yeasts, particularly species within *Saccharomyces. Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term "prokaryotes" refers to hosts such as *E. coli, Lactobacillus, Lactococcus, Salmonella, Streptococcus, Bacillus subtilis* or *Streptomyces*. Also these hosts are contemplated within the present invention.

The term "higher eukaryote" refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term "recombinant polynucleotide or nucleic acid" intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "recombinant host cells", "host cells", "cells", "cell lines", "cell cultures", and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term "replicon" is any genetic element, e.g., a plasmid, a chromosome, a virus, a cosmid, etc., that behaves as an autonomous unit of polynucleotide replication within a cell; i.e., capable of replication under its own control.

The term "vector" is a replicon further comprising sequences providing replication and/or expression of a desired open reading frame.

The term "control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences which govern secretion.

The term "promoter" is a nucleotide sequence which is comprised of consensus sequences which allow the binding of RNA polymerase to the DNA template in a manner such that mRNA production initiates at the normal transcription initiation site for the adjacent structural gene.

The expression "operably linked" refers to a juxtaposition wherein the components so described are in a relationship permitting them to function in their intended manner. A control sequence operably linked' to a coding sequence is ligated in such a way that expression of the coding sequence is achieved under conditions compatible with the control sequences.

An "open reading frame" (ORF) is a region of a polynucleotide sequence which encodes a polypeptide and does not contain stop codons; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term "immunogenic" refers to the ability of a substance to cause a humoral and/or cellular response, whether alone or when linked to a carrier, in the presence or absence of an adjuvant.

"Neutralization" refers to an immune response that blocks the infectivity, either partially or fully, of an infectious agent. A "vaccine" is an immunogenic composition capable of eliciting protection against malaria, whether partial or complete. A vaccine may also be useful for treatment of an infected individual, in which case it is called a therapeutic vaccine.

The term "therapeutic" refers to a composition capable of treating malaria infection such that the severity, symptoms, or pathology of the disease are reduced.

The term "effective amount" for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of immunogen for prophylaxis of malaria disease are about 0.01 to 1000 ug/dose, more preferably about 0.1 to 100 ug/dose, most preferably about 10-50 ug/dose. Several doses may be needed per individual in order to achieve a sufficient immune response and subsequent protection against malaria.

The methods described herein are exemplified for *P. falciparum*, more specifically for NF54 wild type. However, it is understood that other strains of *Plasmodium* may be a suitable sources for the practice of the present invention.

The present invention relates to a composition comprising isolated stage-specific parasites. Even though the description that follows discusses sporozoites in particular, it is understood that the description applies to other stage-specific *Plasmodium* parasites isolated using the method described herein.

In one embodiment of the present invention, the method is described for the wild type NF54-DHFR-GFP strain of *P. falciparum* created by LTC Mike O'Neil at WRAIR in 2008, and has been maintained in settled erythrocyte culture in the presence of drug WR99210. This strain expresses a transgenic GFP (green fluorescent protein) gene that facilitates simple visual monitoring of growth. Briefly, the strain NF54-DHFR-GFP uses a WR99210-resistant allele of DHFR coupled to GFP so that when WR99210 is applied to a parasite population, only those parasites with the inserted resistant allele (and the GFP) survive, thereby selecting specifically for transformed parasites (WR99210 inhibits the protein DHFR which is necessary for parasite survival).

It is envisioned that any gametocyte-producing *Plasmodium* strain, e.g. NF54, 3D7 or other *P. falciparum* line that is able to produce gametocytes in adequately high numbers, could be used in this system, including other strains where gametocytes cannot be produced in blood-stage culture but must be taken from human donors or gametocytes which form in blood stage culture but have difficulty infecting mosquitoes. The sporozoite yield may be affected by the type of parasite put into the system and the performance of any given strain would require some experimentation.

The gametocytes are produced using standardized procedures routinely used in the laboratory (Williams, J L 1999, Am. J. Trop. Med. Hyg. 60:7-13; Trager W and Jensen JB, 1976, Science 193:673-5). Immature gametocytes, primarily stages II-IV, are isolated by magnetic enrichment techniques (Ribault et al. 2008, Malaria J. 7:45). Alternatively, separation can be by gradient separation (Ribault et al., 2008, supra). In a preferred embodiment, the magnetic separation column is the LS column (MACS LS separation columns, Miltenyi Biotec, Germany) together with a flow restrictor (e.g. a 21 or 25 gauge needle). The culture is passed over the column a few times in order to improve gametocyte yield. Other columns can be used for example, LD, XS (Miltenyi Biotec, Germany). Cells that contain parasites are attracted to the magnetic column because parasites sequester iron molecules. Non-adherent cells are any cells without parasites and, therefore, no magnetic capability. After the non-adherent cells are rinsed away, the column is removed from the magnetic field and the adherent material is eluted. In one embodiment, eluent is 10% human serum RPMI 1640 culture medium and gentamicin to a final concentration of about 100 ug/ml. Serum and RPMI were used as parasite growth media and gentamycin was used to prevent bacterial contamination. Others in the art can use other growth media, even saline, whether or not supplemented with antibiotic, to grow the parasites. The eluted material contains pigmented parasites (gametocytes stage II-IV) along with pigmented debris resulting from asexual parasite growth and a small percentage of trophozoites, about 5-10% of the total parasites eluted from the column. The number of stage II-IV gametocytes obtained is calculated using methods known in the art, e.g. a hemocytometer. The number of stage II-IV gametocytes is adjusted to about $1 \times 10^6$ per ml in culture medium, or a density at which the parasites grow best. The gametocytes are returned to culture to rest at 37° C. in a tissue culture flask purged with about 5% $CO_2$, about 5% $O_2$, and about 90% $N_2$ for about 2-3 days). After about 2-3 days, or when stage V gametocytes are formed, exflagelation of mature stage V gametocytes is initiated by addition of xanthurenic acid (XA) to a final concentration of about 1 mM to the culture and incubated at 27° C. Instead of incubating in a flask with ventilation in an incubator environment with constantly maintained 14-21% $O_2$ and 1-5% $CO_2$ as is known in the art, the incubation is done in a flask that is gassed initially and then closed off to the external environment. The incubator used to maintain temperature is kept under atmospheric conditions.

Instead of the traditional method (McClean et al., 2010, *The American Journal of Tropical Medicine and Hygiene* 83:1183-1186) of applying XA transiently then pelleting the parasites and resuspending in fresh media, the present method differs in that the culture is left as-is after XA addition, i.e. the XA is never removed from the culture. Maturing parasites are incubated at 27° C. in a tissue culture flask purged with 5% $CO_2$, 5% $O_2$ and 90% $N_2$ for the rest of the culture period. Sampling or monitoring the cultures by opening flasks is limited, preferably to 2 times at most so as not to expose to air and disrupt the gas mixture of the flask's own environment. Oocysts are detectable after about 6-10 days of culture and easily identifiable at about 14 days by light and influorescent microscopy with an inverted fluorescent scope. Sporozoites can be observed within 21-28 days post xanthurenic acid by light microscopy. Sporozoite presence can be confirmed, for example, by staining with a circumsporozoite protein antibody. Parasite viability can be confirmed, for example, by liver-stage schizont development in a HC-04 invasion assay (Sattabongkot J. et al., 2006, Am. J. Trop. Med. Hyg. 74:708-15). The yield range varies from $4.8 \times 10^3$ to $1.4 \times 10^4$ sporozoides/ml.

Because the sporozoites were grown in media, insect-free and cell-free, the resulting isolated sporozoites are devoid of any insect component and are therefore have zero percent insect material contamination.

The sporozoites can then be preserved. In an embodiment, the sporozoites are cryopreserved, preserved by lyophilization, or preserved by refrigeration. Other methods of preservation are known to those skilled in the art.

The present invention relates to isolated sporozoites for use as a vaccine or an attenuated vaccine. Isolated sporozoites provide the opportunity to study the characteristics of sporozoite genes for the purpose of generating mutant organisms. Methods for attenuating organisms for vaccine purposes are known in the art. For example, sporozoites can be attenuated by genetically engineering a specific mutation in a gene that weakens the parasite and preferably renders it incapable of replicating. An alternate promising strategy is to generate nonreversible genetically defined attenuated parasites by deleting known essential genes. The attenuated parasites are alive and able to effectively stimulate the immune system. Other forms of attenuation include gamma irradiation, long-term in vitro culture, selection for temperature sensitivity, chemical mutagenesis, or silencing the corresponding mRNA translated into proteins, via RNA interference (RNAi).

Sporozoite antigens, or other stage-specific parasite antigens, of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

The immunoassay methods according to the present invention utilize sporozoite domains that maintain linear (in case of peptides) and conformational epitopes (proteins) recognized by antibodies in the sera from individuals infected with a malaria parasite. Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

For in vitro detection of malaria antibodies present in a biological sample, the assay may comprise at least (i) contacting said biological sample with a composition comprising any of the sporozoite proteins or peptides derived from said protein which are immunologically identifiable with a sporozoite, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, and (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from *Plasmodium* with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, and possibly also including an automated scanning and interpretation device for inferring the malaria parasite present in the sample from the observed binding pattern.

The sporozoite proteins, peptides, or antigens of the present invention will typically be packaged in the form of a kit for use in these immunoassays. The kit will normally contain in separate containers the sporozoite antigen, control antibody formulations (positive and/or negative), labeled antibody when the assay format requires the same and signal generating reagents (e.g. enzyme substrate) if the label does not generate a signal directly. The sporozoite antigen may be already bound to a solid matrix or separate with reagents for binding it to the matrix. Instructions (e.g. written, tape, CD-ROM, etc.) for carrying out the assay usually will be included in the kit.

Immunoassays that utilize the sporozoite antigen are useful in screening blood for the preparation of a supply from which potentially infective malaria parasite is lacking. The method for the preparation of the blood supply comprises the following steps: reacting a body component, preferably blood or a blood component, from the individual donating blood with sporozoite proteins of the present invention to allow an immunological reaction between malaria antibodies, if any, and the sporozoite antigen; and detecting whether anti-malaria antibody—sporozoite antigen complexes are formed as a result of the reacting. Blood contributed to the blood supply is from donors that do not exhibit antibodies to the native sporozoite antigens.

The present invention further contemplates the use of sporozoite proteins, or parts thereof as defined above, for in vitro monitoring of the exposure to malaria infection resulting from *P. falciparum* parasites or prognosing the response to treatment (for instance with chloroquine, mefloquine, Malarome) of patients suffering from malaria infection comprising:

incubating a biological sample from a patient with malaria infection with an sporozoite protein or a suitable part thereof under conditions allowing the formation of an immunological complex, removing unbound components, calculating the anti-sporozoite titers present in said sample (for example at the start of and/or during the course of therapy), and monitoring the natural course of malaria infection, or prognosing the response to treatment of said patient on the basis of the amount anti-sporozoite titers found in said sample at the start of treatment and/or during the course of treatment.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one sporozoite peptide as defined above, a buffer or components necessary for producing the buffer enabling the binding reaction between these proteins or peptides and the anti-sporozoite antibodies present in a biological sample, means for detecting the immune complexes formed in the preceding binding reaction, and possibly also an automated scanning and interpretation device for inferring a decrease of anti-sporozoite titers during the progression of treatment.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The present invention also relates to a sporozoite specific antibody raised upon immunizing an animal with a peptide or protein composition, with said antibody being specifically reactive with any of the polypeptides or peptides as defined above, and with said antibody being preferably a monoclonal antibody.

The present invention also relates to a sporozoite specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The sporozoite specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from one or more certain strains may be used as a medicament, more particularly for incorporation into an immunoassay for the detection of *Plasmodium* strains for detecting the presence of sporozoite antigens, or antigens containing sporozoite epitopes, for prognosing/monitoring of malaria disease, or as therapeutic agents.

Alternatively, the present invention also relates to the use of any of the above-specified sporozoite monoclonal antibodies for the preparation of an immunoassay kit for detecting the presence of sporozoite antigen or antigens containing sporozoite epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least (i) contacting said biological sample with any of the sporozoite specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, and (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of sporozoite-specific antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to sporozoite, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-sporozoite response (Linthicum, D. S. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

In another aspect of the invention is provided a DNA vaccine against *P. falciparum* malaria comprising a nucleic acid encoding one or more sporozoite antigens or all or parts of a sporozoite genome. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

Therefore, the present invention relates to a DNA or cDNA segment which encodes the sporozoite genome or parts thereof as described above. Genome sequences from different strains of *Plasmodium* have been published and are publicly available. Other strains of *P. falciparum* are expected to contain sequences at least 90% identical which will likely produce antigens capable of eliciting protective/neutralizing antibodies.

DNA or nucleic acid sequences to which the invention also relates include fragments of the sporozoite DNA containing protective epitopes or antigenic determinants. Such epitopes may be linear or conformational as shown below in the Examples. The sequence of nucleic acids encoding antigens may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. It is understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the genes of P. falciparum sporozoite are equivalents within the scope of the present invention.

The DNA encoding the desired antigen can be introduced into the cell in any suitable form including, the fragment alone, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual or DNA Cloning*, Vol. I and II (D. N. Glover, ed., 1985) for general cloning methods.

The DNA, alone or in a vector, can be delivered by injection into the tissue of the recipient, oral or pulmonary delivery and inoculation by particle bombardment (i.e., gene gun) after coating a carrier particle with the DNA vaccine. Any of these methods can be used to deliver DNA as long as the DNA is expressed and the desired antigen is made in the cell.

Generally, the DNA vaccine administered may be in an amount of about 1-5 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The present invention more particularly relates to a composition comprising at least one of the above-specified peptides or a recombinant sporozoite protein composition as defined above, for use as a vaccine for immunizing a mammal, preferably humans, against malaria, comprising administering a sufficient amount of the composition possibly accompanied by pharmaceutically acceptable adjuvant(s), to produce an immune response. The vaccine composition of the present invention is expected to provide cross-protection against infection from other P. falciparum malaria strains.

Immunogenic compositions can be prepared according to methods known in the art. The present compositions comprise an immunogenic amount of a recombinant sporozoite proteins or peptides as defined above, usually combined with a pharmaceutically acceptable carrier, preferably further comprising an adjuvant.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine(nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The sporozoite protein of the invention may also be incorporated into Immune Stimulating Complexes together with saponins, for example QuilA (ISCOMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present other P. falciparum antigens for inclusion into a multi-antigen subunit vaccine (e.g. other malaria antigens, such as AMA, Pfs25. In this use, the proteins of the invention provide an immunogenic carrier capable of stimulating an immune response to other antigens. The antigen may be conjugated either by conventional chemical methods, or may be cloned into the gene encoding a sporozoite antigen fused to the 5' end or the 3' end of the sporozoite antigen gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the compounds, or vaccines, disclosed herein may be carried out by any suitable means, including parenteral injection (such as intraperitoneal, subcutaneous, or intramuscular injection), The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

In vitro production of sporogonic *P. falciparum*

*P. falciparum* NF54 or NF54-GFP strain was grown via standard methods (Trager and Jensen, 1976, supra; Zolg, et al., 1982, J. Parasitol. 68, 1072-1080). Gametocytes were purified via magnetic column and seeded into 25 cm$^2$ flasks. Cultures were maintained first at 37° C., then at 27° C. Parasite development was monitored via an inverted epifluorescent microscope.

Microscopy

Parasites were visualized and imaged 1) "as is" through the flask or in a hemocytometer using phase contrast microscopy or epifluorescent detection of GFP; 2) in a hemocytometer following trypan blue staining for vital exclusion; 3) fixed to a glass slide and stained with 10% Giemsa. Live video imaging of sporozoite motility in flask was also obtained.

Immunofluorescence Assay 10 uL of cultured sporozoites was aliquoted from liver cell assay preparation, applied to glass slides and fixed with methanol. Slides were blocked with BSA then stained with anti-CSP as the primary antibody and AlexaFluor488 anti-IgG as the secondary. Slides were mounted using Vectashield plus DAPI (Vector Laboratories) and visualized with epifluorescent microscopy.

EXAMPLE 1

Producing *Plasmodium falciparum* Mosquito-Stage Parasites in an In Vitro Culture System Outside the Mosquito Midgut.

Figure 1:
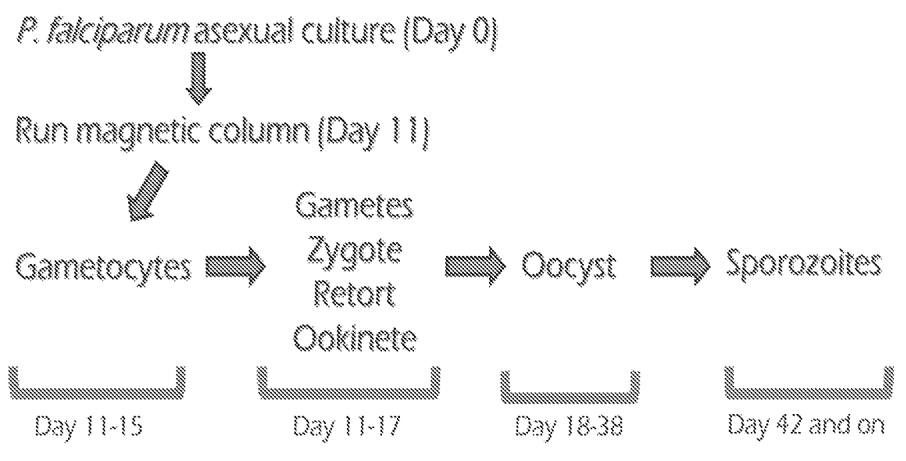

The NF54-DHFR-GFP strain of *P. falciparum* was created by LTC Mike O'Neil at WRAIR in 2008, and has been maintained in settled erythrocyte culture in the presence of drug WR99210. The gametocytes are produced using standardized procedures routinely used in our laboratory (Williams 1999, supra). Immature gametocytes are isolated by magnetic enrichment techniques (Ribault et al. 2008, supra). The optimal magnetic separation column is the LS column (MACS LS separation columns, Miltenyi Biotec, Germany) together with a flow restrictor (i.e. a 21 or 25 gauge needle. The culture is passed over the column three times to improve yield. After the non-adherent cells are rinsed away, the column is removed from the magnetic field and the adherent material is eluted with 10% human serum RPMI 1640 culture medium and gentamicin to a final concentration of 100 ug/ml. The eluted material contains pigmented parasites (gametocytes stage II-IV, see FIG. 1, Culture Progression) along with trophozoite stage parasites and pigmented debris resulting from asexual parasite growth. The number of stage II-IV gametocytes obtained is calculated using hemocytometer counts and adjusted to 1×10$^6$ per mL in RPMI culture medium. The gametocytes are returned to culture for rest at 37° C. in a tissue culture flask purged with about 5% CO$_2$, about 5% O$_2$, and about 90% N$_2$ for about 2-3 days. After about 2-3 days, exfalaggelation of mature stage V gametocytes is initiated by addition of xanthurenic acid (XA) to a final concentration of 1 mM and incubated at 27° C. Oocysts are detectable after 10 days of culture and easily identifiable at 14 days by light (data not shown) and inflourescent microscopy (data not shown) with an inverted fluorescent scope. Sporozoites can be observed within 21-28 days post xanthurenic acid by light microscopy. Sporozoite presence was confirmed by staining with an anti-circumsporozoite protein (data not shown) and parasite viability was confirmed by liver-stage schizont development in a HC-04 invasion assay.

EXAMPLE 2

Functional Assay 1: Liver Cell Invasion Assay

Invasion assay was performed as described by Sattabongkot, J. et al. (2006, Am. J. Trop. Med. Hyg. 74, 708-715. HC-04 monolayers were prepared by seeding ~60,000 cells into individual wells of Permanox Labtek chamber slides (Thermo Fisher Scientific, Waltham, Mass.). Sporozoites were concentrated by centrifugation and 30,000-80,000 sporozoites (depending on replica) were applied to monolayer; PBS was applied to at least one well per replica as a negative control. After a 3-hr incubation, free sporozoites were removed by washing 3 times with complete media. Slides were incubated at 37° C. with 5% $CO_2$ and media was changed daily. On day 5-6, slides were fixed with cold methanol, blocked with BSA and stained with anti-HSP-70 as the primary antibody and AlexaFluor488 anti-IgG as the secondary.

Slides were mounted using Vectashield plus DAPI (Vector Laboratories, Burlingame, Calif.). Growth of sporozoites into exo-erythrocytic forms was observed using epifluorescent microscopy in 5 biological replicates.

Our results showed that two different cultured sporozoites uniformly express circumsporozoite protein (CSP) on their surface and that parasites are capable of invading and developing inside hepatic cells (HC-04 cells, two different replicate cultures on day 6) (data not shown).

What is claimed is:

1. A method for producing *Plasmodium* sporozoites in vitro in a cell-free and mosquito-free environment, comprising
   (i) isolating *Plasmodium* gametocytes to produce a gametocyte culture in vitro,
   (ii) incubating the gametocyte culture in vitro in the presence of xanthurenic acid at a temperature of 37° C. for 24 hours,
   (iii) incubating the gametocyte culture of step (ii) in vitro in the presence of xanthurenic acid at a temperature of 27° C., under conditions that mature sporozoites are formed, and
   (iv) isolating the mature sporozoites in vitro.

2. The method according to claim 1 wherein in step (i) the gametocytes are isolated from a *Plasmodium* erythrocyte culture.

3. The method according to claim 1 wherein in step (iv) the culture is progressed to sporozoites by exflagellation.

4. The method of claim 1 wherein said xanthurenic acid in step (iii) is added at 100 mM.

5. The method of claim 1 wherein in step (ii) gantamycin is added to the culture.

6. The method of claim 1 wherein the xanthurenic acid in step (ii) is added at 1 mM.

7. The method of claim 1 wherein the mature sporozoites produced in step (iv) are infectious and metabolically active.

8. The method of claim 1 wherein the mature sporozoites produced in step (iv) are free of insect material.

* * * * *